US007876453B1

(12) United States Patent
Williams et al.

(10) Patent No.: US 7,876,453 B1
(45) Date of Patent: Jan. 25, 2011

(54) LASER ULTRASONIC MULTI-COMPONENT IMAGING

(75) Inventors: Thomas K. Williams, Federal Way, WA (US); Kenneth Telschow, Des Moines, WA (US)

(73) Assignees: The Boeing Company, Chicago, IL (US); Battelle Energy Alliance, LLC, Idaho Falls, ID (US)

(*) Notice: Subject to any disclaimer, the term of this patent is extended or adjusted under 35 U.S.C. 154(b) by 447 days.

(21) Appl. No.: 12/017,726

(22) Filed: Jan. 22, 2008

(51) Int. Cl.
*G01B 9/02* (2006.01)
(52) U.S. Cl. ................................................ 356/502
(58) Field of Classification Search ................ 356/502, 356/432
See application file for complete search history.

(56) References Cited

U.S. PATENT DOCUMENTS 7,649,632 B2 * 1/2010 Murray ........................ 356/502
2009/0168074 A1 * 7/2009 Monchalin et al. ........... 356/502

FOREIGN PATENT DOCUMENTS

WO    WO2005094503    * 10/2005

OTHER PUBLICATIONS

Mukadadi et al., "Off-Axis Propagation of Ultrasonic Guided Waves in Thin Orthotropic Layers: Theorectical Analysis and Dynamic Holographic Imaging Measurements", IEEE Trans. Ultrasonics, Ferroelectrics and Freg Control, Nov. 2001, 48(6), 51 pgs.
Telschow et al., "Direct Imaging of Traveling Lamb Waves in Plates Using Photorefractive Dynamic Holography", J. Acoust. Soc. Am, 106(5), Nov. 1999, pp. 2578-2587.
Telschow et al., "Full-Field Imaging of GHz Film Bulk Acoustic Resonator Motion", IEEE Transactions Ultrasonics, Ferroelectrics and Freg Control , vol. 50, Issue 10, Oct. 2003, 8 pgs.
Telschow et al., "Imaging Anisotropic Elastic Properties of an Orthotropic Paper Sheet Using Photorefractive Dynamic Holography", Ultrasonics 40, Dec. 2002, pp. 1025-1035.
Telschow et al., "Imaging Laser Ultrasonics Measurement of the Elastodynamic Properties of Paper", IEEE 2001 Ultrasonics Symposium, Oct. 2001, 9 pgs.
Telschow et al., "Material Property Measurement of Metallic Parts Using the INEEL Laser Ultrasonic Camera", Aug. 1999, Intl Symposium on Advanced Sensors for Metals Processing, 38th Annual Conf of Metallu, 11 pgs.

* cited by examiner

*Primary Examiner*—Hwa S. A Lee
(74) *Attorney, Agent, or Firm*—Lee & Hayes, PLLC

(57) ABSTRACT

Techniques for ultrasonic determination of the interfacial relationship of multi-component systems are discussed. In implementations, a laser energy source may be used to excite a multi-component system including a first component and a second component at least in partial contact with the first component. Vibrations resulting from the excitation may be detected for correlation with a resonance pattern indicating if discontinuity exists at the interface of the first and second components.

16 Claims, 5 Drawing Sheets

LASER ULTRASONIC MULTI-COMPONENT IMAGING

GOVERNMENT RIGHTS

The subject matter of this application was made with United States Government support under DE-AC07-051D14517 awarded by the United States Department of Energy. The United States Government has certain rights in this invention.

TECHNICAL FIELD

The present disclosure relates to systems and methods for providing minimal contact or non-contact ultrasonic evaluation of the interface between components in a multi-component system.

BACKGROUND

Often coated substrates are formed from multiple components. Take for example, aerospace applications. Aircraft often will have skins or outer surfaces which are attached to the structural support members via fasteners, such as rivets, screws or the like. In this situation, fasteners which are suitably secured for the fasteners primary purpose, may impact the final appearance of a subsequently applied coating. For example, a slightly gapped fastener-head, which is capable of performing the fastener's primary purpose, may nonetheless affect the overall finish of a coating which covers the fastener and material forming the outer skin. The coating may experience "paint wicks" or other defects which may impact the performance of the coating system or may merely be visually unappealing. For instance, an applied coating may enter a gapped space at the fastener/outer surface interface. While the coating may be treated to correct the visually unappealing area, these procedures are typically time consuming and may require skilled personnel attention.

Contact evaluation methodologies, such as the use of feeler gauges, are time consuming and may be used intermittently as a spot check on a representative number of fastener. Contact evaluation is time consuming as the gauge is placed in contact between the fastener and the member being secured by the fastener.

SUMMARY

Techniques for ultrasonic determination of the interfacial relationship of multi-component systems are discussed. In implementations, a laser energy source may be used to excite a multi-component system including a first component and a second component at least in partial contact with the first component. Vibrations resulting from the excitation may be detected for correlation with a resonance pattern and/or wavefront properties indicating if discontinuity exists at the interface of the first and second components.

This Summary is provided to introduce various concepts and features in a simplified form that are described below in the Detailed Description. This Summary is not intended to identify key or essential features of the claimed subject matter, nor is this summary intended to be used as an aid in determining the claimed subject matter.

BRIEF DESCRIPTION OF THE DRAWINGS

Embodiments of systems and methods in accordance with the teachings of the present disclosure are described in detail below with reference to the following drawings.

DETAILED DESCRIPTION

Figure 1:
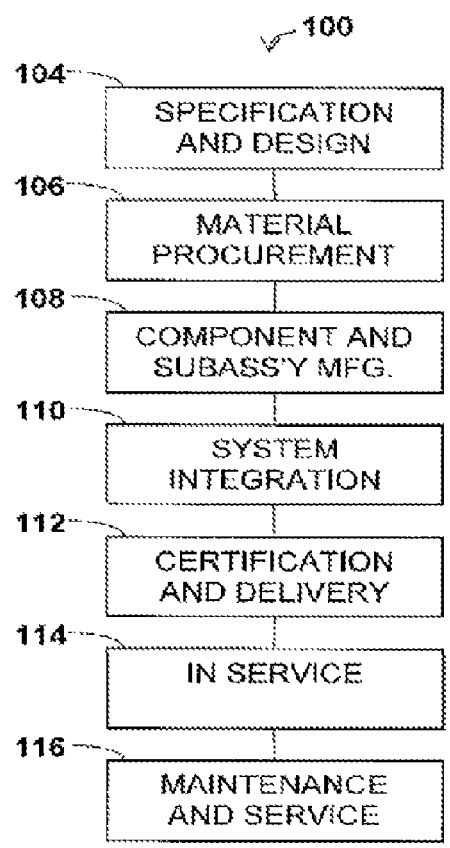
FIG. 1 is a flow diagram of aircraft production and service methodology.
Figure 2:
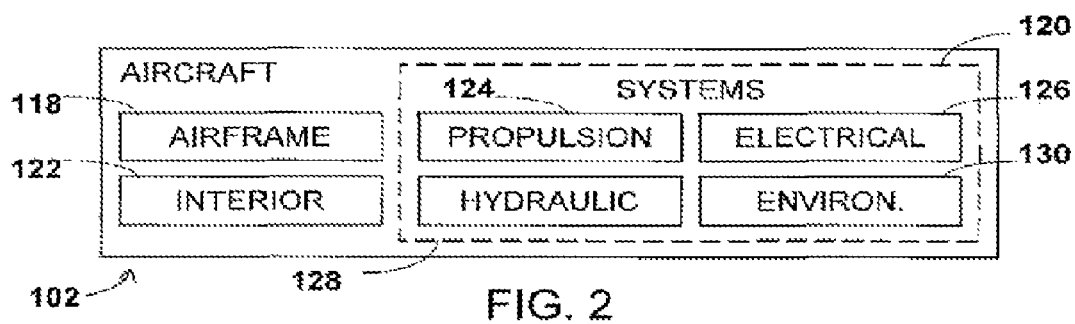
FIG. 2 is a block diagram of an aircraft.
Figure 3A:
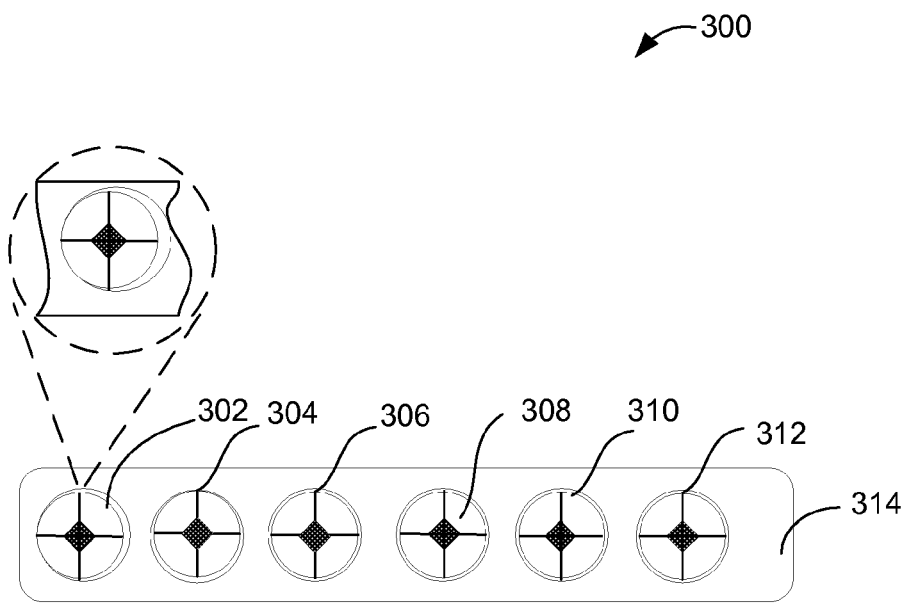
FIG. 3A is an overhead plan view of a sample system.
Figure 3B:
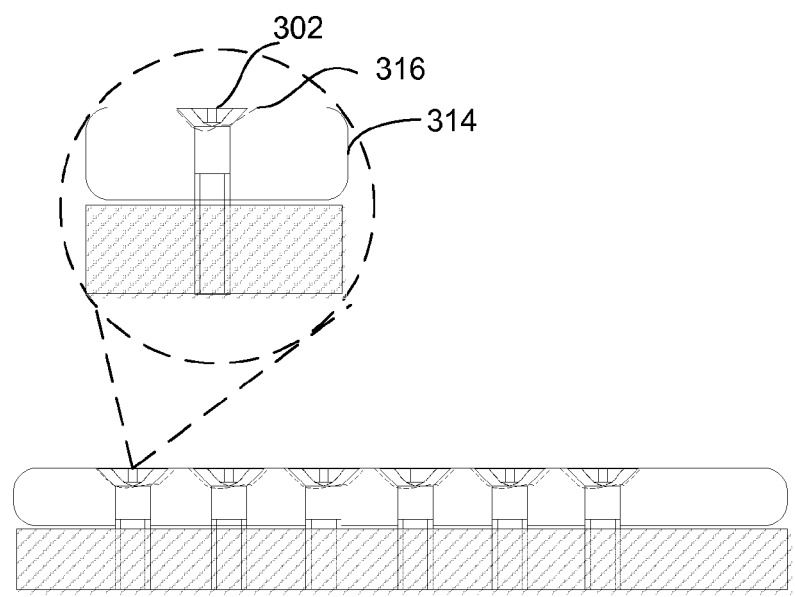
FIG. 3B is an cross-sectional view of a sample system.
Figure 4A:
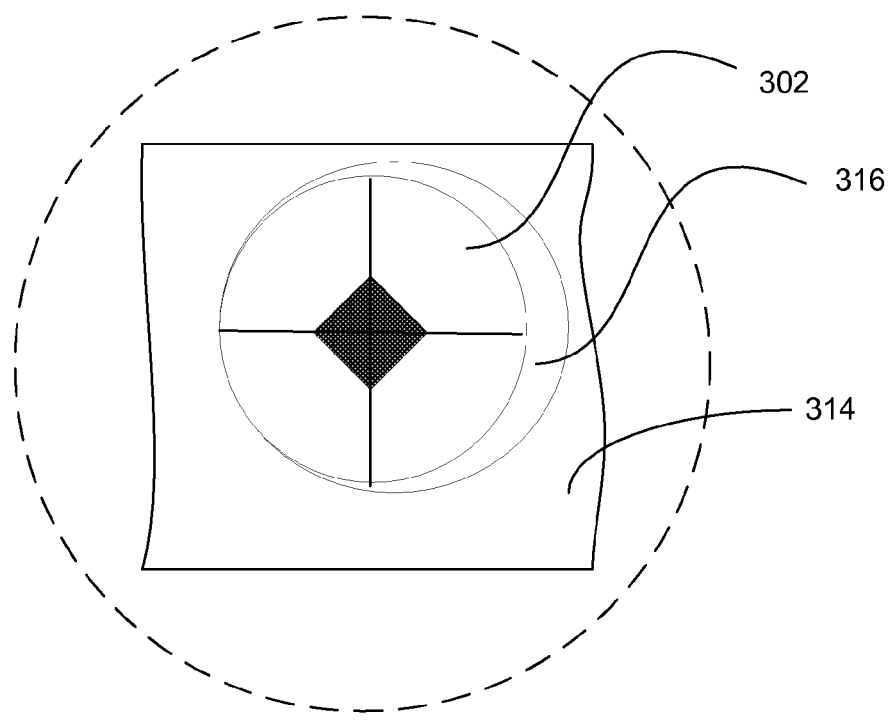
FIG. 4A is an enlarged overhead plan view of a gapped fastener included in FIG. 3A.
Figure 4B:
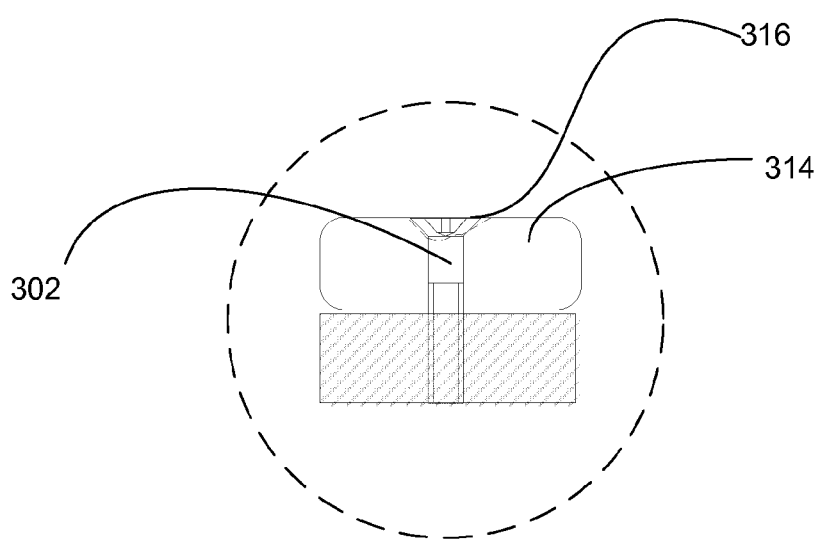
FIG. 4B is an enlarged cross-sectional view of a gapped fastener included in FIG. 3B.

Referring more particularly to the drawings, embodiments of the disclosure may be described in the context of an aircraft manufacturing and service method 100 as shown in FIG. 1 and an aircraft 102 as shown in FIG. 2. During pre-production, exemplary method 100 may include specification and design 104 of the aircraft 102 and material procurement 106. During production, component and subassembly manufacturing 108 and system integration 110 of the aircraft 102 takes place. Thereafter, the aircraft 102 may go through certification and delivery 112 in order to be placed in service 114. While in service by a customer, the aircraft 102 is scheduled for routine maintenance and service 116 (which may also include modification, reconfiguration, refurbishment, and so on).

Each of the processes of method 100 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 2, the aircraft 102 produced by exemplary method 100 may include an airframe 118 with a plurality of systems 120 and an interior 122. Examples of high-level systems 120 include one or more of a propulsion system 124, an electrical system 126, a hydraulic system 126, and an environmental system 130. Any number of other systems may be included. Although an aerospace example is shown, the principles of the invention may be applied to other industries, such as the automotive industry.

Apparatus and methods embodied herein may be employed during any one or more of the stages of the production and service method 100. For example, components or subassemblies corresponding to production process 108 may be fabricated or manufactured in a manner similar to components or subassemblies produced while the aircraft 102 is in service. Also, one or more apparatus embodiments, method embodiments, or a combination thereof may be utilized during the production stages 108 and 110, for example, by substantially expediting assembly of or reducing the cost of an aircraft 102. Similarly, one or more of apparatus embodiments, method embodiments, or a combination thereof may be utilized while the aircraft 102 is in service, for example and without limitation, to maintenance and service 116.

Accordingly, techniques and systems for providing non-contact or minimal contact evaluation of components in multi-component systems including the interfacial relationship between components within the system are discussed. In embodiments, the techniques and systems discussed herein may be used to determine the existence of gaps or voids occurring at the interface between fasteners and aerospace outer skins including maintenance related evaluation. For example, the techniques discussed herein may be used to identify gaps or other interface anomalies occurring between fasteners and the material forming the outer surface of a vehicle, such as an aerospace vehicle.

While implementations relating to the aerospace industry are discussed, the principles and techniques may be utilized in other fields such as the automotive field, marine transportation, and so on in which the interfacial relationship between components is at issue. Although reference is made to a conventional aircraft system including a metal fastener used to secure a metal alloy skin, such as an aircraft aluminum alloy 2024, the principles are suitable for use with various constituent materials, including alloys, composite materials, and the like. In implementations, the subject system may be coated, partially coated or uncoated. Exemplary coatings may include, but are not limited to, conversion coatings (in which the surface of the material is chemically treated to so as to alter the surface region's chemical composition), base coatings, top coatings, multi-layer coating systems, and so on.

Referring to FIGS. 3A through 6, systems for ultrasonic imaging and multi-component subject systems 300 (samples) are discussed with respect to techniques for analyzing the interface region of components in multi-component systems. For example, an ultrasonic imaging system 500 (highly diagrammatic) and techniques 600 may be used to examine the interfacial relationship of one or more fasteners (for reference six fasteners, individually, 302-312 are discussed) or second components which extend through a generally planar outer surface 314 (field material) or first component, e.g., a rivet secured through a curved portion of a wing or fuselage. A fastener may extend transversely through the skin and into a support, such as a rib support include in an airframe wing.

For discussion purposes, a fastener 302 may be positioned in a gapped or non-continuous manner with respect to the material forming the field or the outer surface 314 of the vehicle. For example, instead of continuously contacting a countersunk recess formed in the metal sheeting, forming the exterior of the vehicle, the fastener may be slightly gapped 316 so that a void exists at the interface of the fastener and outer skin component in comparison to an aligned fastener. While a fastener in the former configuration may be capable of performing its primary purpose, the gap 316 may result in coating abnormalities which require additional applicator attention or may result in a defect in a coating system. In instances, coatings may wick or result in other coating abnormalities which may impact the overall look and/or performance of the coating system. Coating wicks and other coating inconsistencies may require additional time consuming treatment to remedy the situation.

In maintenance situations, personnel may wish to nondestructively evaluate the components including the interfacial relationship of the components without removing the coating system or check the condition of the subject system once an overlying coating system has been removed. The techniques discussed herein may permit personnel to determine if any corrosion has occurred in the components, including corrosion at the interface of the components in a minimal or non-contact fashion.

Figure 5:
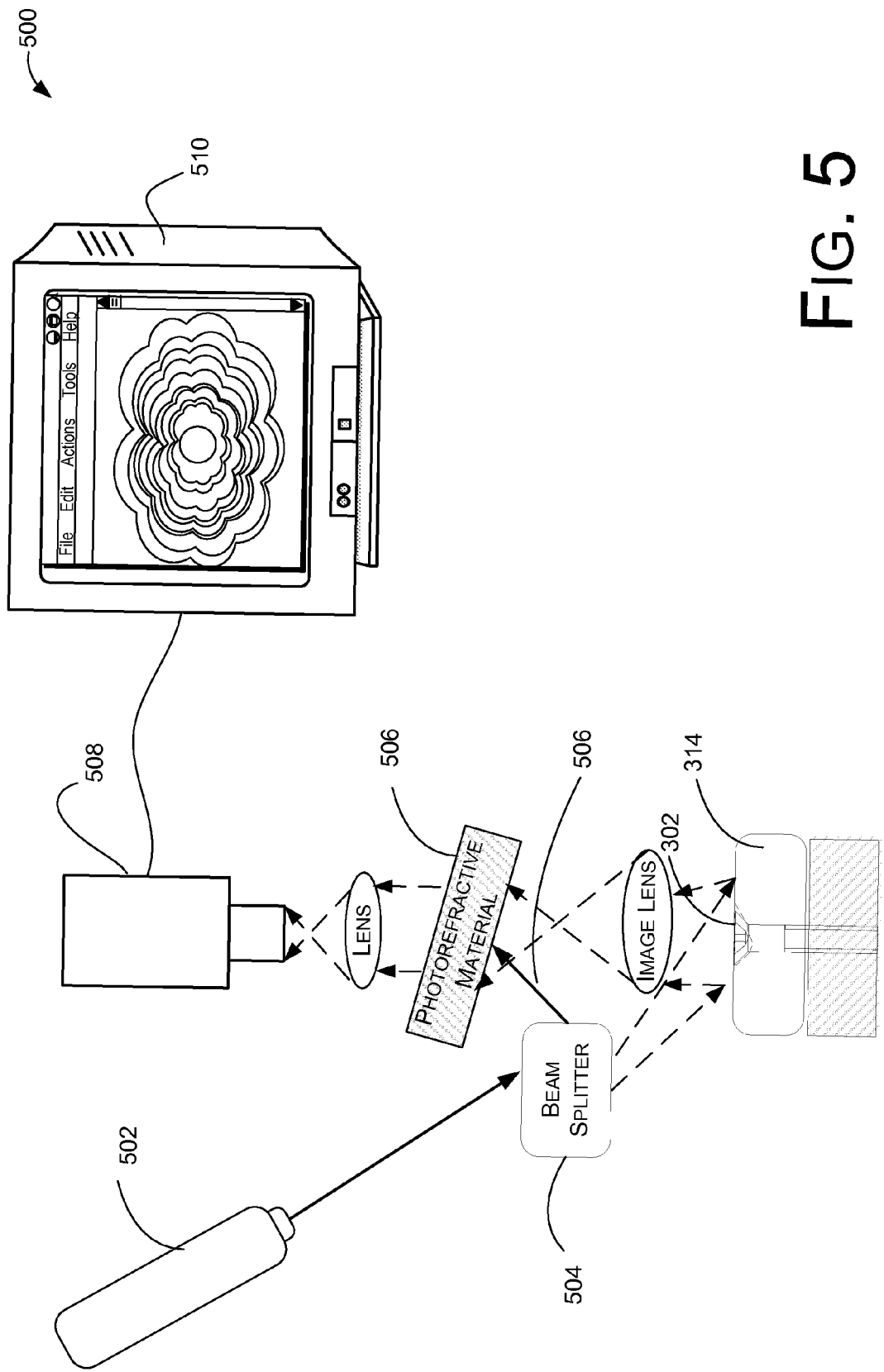
FIG. 5 is a highly diagrammatic plan view of a ultrasonic multi-component imaging system in accordance with an implementation.
Figure 6:
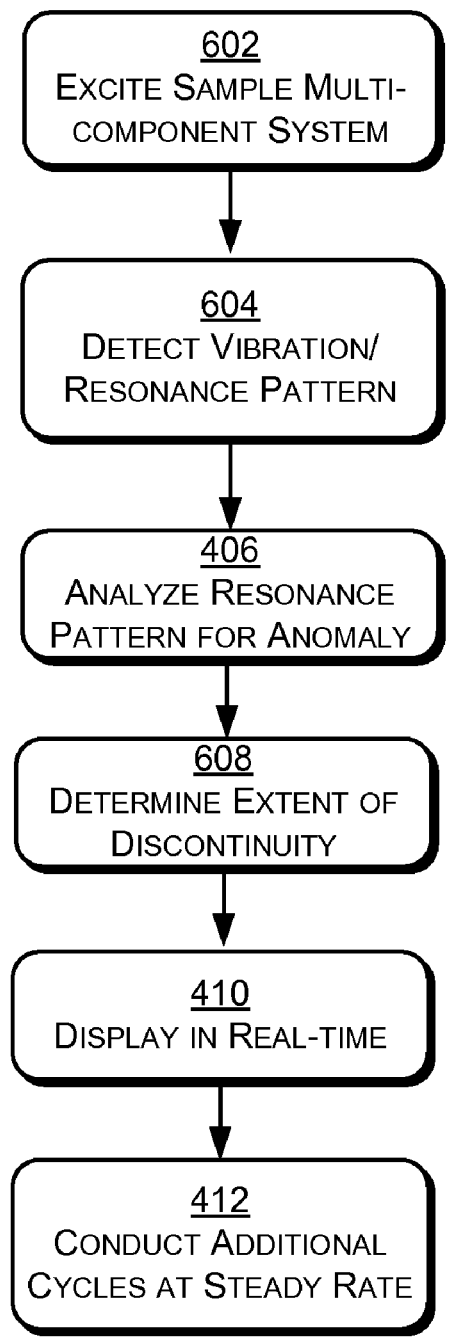
FIG. 6 is a flowchart of technique in accordance with the present disclosure.

With particular reference to FIGS. 5 and 6, in implementations, an energy source, such as a laser source 502, may be used to excite 602 a multi-component sample system (such as multi-component system 300). In embodiments, an energy source such as a laser source 502 may operate in the frequency range of 0.5 MHz (zero point five mega hertz) to 100 MHz (one hundred mega hertz). As will be appreciated, other frequency ranges beyond the aforementioned ranged may be used based on design preferences. For example, frequencies may extend from approximately 0.5 MHz (zero point five mega hertz) the to approximately two gigahertz. For instance, energy in wavelength of approximately 563 nanometers may be used, a helium-neon laser source or the like. The beam of laser energy, used to excite the components (e.g., 302, 314), may be modulated, such as by changing frequencies.

Exemplary ultrasonic wave excitation mechanism may include, but are not limited to, a contact piezoelectric transducer, a noncontacting ElectroMagnetic Acoustic Transducer (EMAT) or an additional pulsed or amplitude modulated laser.

The energy may cause one or more of the components to vibrate or resonate. For example, a fastener 302 may vibrate in an out-of-plane manner in response to the application of a particular energy frequency. In the previous situation, a zone or region including the first component 314 and a second component 302 may be excited with a modulated laser beam such that at least one of the components vibrates in approximately the nanometer range or vibrates sympathetically due to the vibration of an adjacent component which is at least partially in contact with the adjacent vibrating component. For example, a region including a first component and a second component may be energized so that the second component vibrates in an out-of-plane manner by a distance in the nanometer range. The particular range of vibration may vary based on subject system conditions. While the energy beam may be directed generally to a region including the components being evaluated, in other instances the energy beam may be preferentially directed to particular component(s). An example of the foregoing, is directing a laser beam to a primary component (such as the outer surface material), while preventing or minimizing energy directed to secondary components. Conversely, one or more secondary components may be excited while energy is prevented or minimized from energizing a primary component in other situations. For example, the laser beam is directed at a fastener being evaluated.

The energy beam may be split into a reference beam and an energizing beam by a beam splitter 504 (used for energizing the sample or subject multi-component system), so that the reference beam may be used as a reference when determining 506 resultant resonance patterns and/or wavefront properties. For example, the reference beam may be used as a standard or reference when applying a Fourier transform (e.g., a fast Fourier transform (FFT)) in order to calculate the resonance pattern and/or wavefront properties for a first component and second component system.

In the wing skin and fastener example, the modulated laser beam may cause the fastener to vibrate out of plane with respect to a plane generally defined by the outer skin material. The particular frequency or range of energy frequencies implemented may be selected based on the in-question multi-component system (workpiece) parameters including the type of materials, and so on. The laser source may be scanned thorough a range of frequencies as desired or the laser energy may be adjusted based on the multi-component system being evaluated.

A photorefractive material such as a photorefractive crystal 505 may be used in conjunction with determining an image of the vibration associated with the excitation of the sample system. Suitable photorefractive crystals may include, but are not limited to, a bismuth silicon oxide based material and so on exhibiting photorefractive properties. For example, the energy returned, from exciting the sample system, may be directed to the photorefractive crystal along with the reference portion of the energy beam for detection of the wave propagation.

The resultant vibrations, such as via the photorefractive crystal, may be detected 604 via a charge coupled detector 506 or other detector suitable for discerning vibrations (e.g., wavefront), such as ultrasonic vibrations. The component and/or subject system vibrations may be referenced to the reference beam 508 split from the original laser beam used to excite the subject system. The wavefront and/or resonance pattern may be determined so that discontinuities between the components may be identified. In implementations, the resonance pattern and/or wavefront properties may be displayed 610 (such as on a monitor 510) in real-time. For instance, the output may be presented to personnel via a display screen for follow-up evaluation or correction. In other instances, other information associated with the multi-component system evaluation may be presented as well or in place of a visual representation of the resonance pattern and/or wavefront properties.

The vibration waves and resonance pattern for the multi-component system may not be uniform if a region of one of the components is not in uniform intimate contact with the other component. For instance, while the vibration waves may propagate outwardly for portions of the fastener/outer surface material which are in close contact, a gap may cause the fastener vibration wave not to propagate in the direction of the gap or void, do so in a diminished manner or in an otherwise identifiable manner. Additional anomalies, which may be identified based on analysis 406 of the resonance pattern and/or wavefront properties, include, but are not limited to, material strength orientation, grain pattern, a component anomaly (e.g., corrosion, interfacial corrosion, deformation and so on).

The extent of an interfacial discontinuity may be determined 608 from the resonance pattern and/or wavefront properties. In implementations, the ultrasonic imaging system may be configured to determine quantitative factors associated with the anomaly. For example, the size of the gap may be determined with reference to the other portions of the resonance pattern and/or wavefront properties in which the components are in intimate contact.

The excitation and detection cycle may be conducted 612 at a substantially steady rate. For example, an ultrasonic imaging system may be configured to scan a region including the subject components at a substantially steady rate. In the foregoing manner, the system may be mounted on a mobile platform or other mobile base so that multiple regions may be scanned without making discrete evaluations. For example, a system implementing the discussed methods may travel over a wing portion in which a row of fasteners extends along the primary axis of the wing member.

Other suitable techniques include, but are not limited to, Electronic Speckle Pattern Interferometry (ESPI, where one processes the images in a computer) or by scanning a single point laser beam to form an image.

Electronic Speckle Pattern Interferometry or Digital Holographic Imaging illuminates the object with laser light and interferes the reflected light from the object with a reference wavefront at the sensing surface of a video recording device (e.g. Charge Coupled Device camera). If the captured images are synchronized to the acoustic wave excitation then a still interference image may result that can be converted to an image of the ultrasonic wavefront through application of phase-unwrapping with a computer. This technology is commercially available for low frequency operation (usually in the kHz range).

Scanning of a single laser beam (focused to spot) over the surface can also be used to form images through interferometric detection of the acoustic motion at the one spatial point. This technique can scan the laser beam and produce images of the acoustic wavefront.

While specific embodiments of the invention have been illustrated and described herein, as noted above, many changes can be made without departing from the spirit and scope of the invention. Accordingly, the scope of the invention should not be limited by the disclosure of the specific embodiments set forth above. Instead, the invention should be determined entirely by reference to the claims that follow.

What is claimed is:

1. A method for evaluating interface anomalies between components, the method comprising:
    emitting a modulated laser beam at a multi-component system including a first component and a second component which is at least in partial contact with the first component, at least one of the first component and the second component being a fastener;
    exciting at least a portion of the multi-component system via the modulated laser beam; and
    detecting vibrations resulting from the exciting at least a portion of the multi-component system, the vibrations correlating to a resonance pattern indicating a discontinuity between the first component and the second component.

2. The method as described in claim 1, wherein the multi-component system is at least partially coated by at least one of a conversion coating, a base coating or a coating system made of more than one coating layer.

3. The method as described in claim 1, further comprising analyzing the resonance pattern to obtain at least one of a material strength orientation, a grain pattern, or a component anomaly for at least one of the system components.

4. The method as described in claim 1, wherein the exciting at least a portion of the multi-component system excites at least a portion of the multi-component system within the frequency range of between 0.5 MHz (zero point five mega hertz) to 100 MHz (one hundred mega hertz) and the resonance pattern is related to the detected vibrations in the nanometer range.

5. The method as described in claim 1, wherein:
    the first component is the fastener and the second component is an outer skin material; and
    the resonance pattern indicating a gap occurring at an interface between the fastener and the outer skin material.

6. The method as described in claim 1, wherein the detecting the vibrations detects the vibrations via a photorefractive crystal to present the resonance pattern in real-time.

7. The method as described in claim 1, wherein the resonance pattern is based on an out of plane vibration of the second component extending generally transversely, with respect to a plane defined by the first component.

8. The method as described in claim 6, wherein the presenting the resonance pattern in real-time presents the resonance pattern as a digital holographic image.

9. A method for identifying interface anomalies between vehicle components, the method comprising:
    emitting a laser beam at a multi-component vehicle system including a fastener and an outer skin material;
    exciting one or more of the fastener and the outer skin material via the laser beam;

detecting vibrations resulting from the exciting one or more of the fastener and the outer skin material; and presenting a resonance pattern identifying a gap between the fastener and the outer skin material of the multi-component vehicle system, the resonance pattern based on the detected vibrations.

10. The method as described in claim 9, further comprising determining a size of the gap between the fastener and the outer skin material of the multi-component vehicle system.

11. The method as described in claim 9, further comprising splitting the laser beam into a reference beam and an energizing beam, the energizing beam directed at or more of the fastener and the outer skin material.

12. The method as described in claim 11, wherein the resonance pattern is further based on the reference beam.

13. The method as described in claim 9, wherein the multi-component vehicle system is an aerospace vehicle, the outer skin material is a material forming an outer surface of the aerospace vehicle, and the fastener secures the material forming the outer surface of the aerospace vehicle to a support component of the aerospace vehicle.

14. The method as described in claim 9, wherein the exciting one or more of the fastener and the outer skin material via the laser beam comprises one of:
 exciting a region of the multi-component vehicle system including both the fastener and the outer skin material;
 exciting only the fastener; or
 exciting only the outer skin material.

15. The method as described in claim 9, wherein the emitting the laser beam causes the fastener to vibrate out of plane with respect to a plane generally defined by the outer skin material.

16. The method as described in claim 9, wherein:
 the detecting the vibrations detects the vibrations via a photorefractive crystal; and
 the presenting the resonance pattern presents the resonance pattern in real-time as a digital holographic image.

\* \* \* \* \*